(12) United States Patent
Couts

(10) Patent No.: US 8,499,762 B2  
(45) Date of Patent: Aug. 6, 2013

(54) APPARATUS FOR ALLEVIATING PRESSURE ON EARS WHILE USING OXYGEN

(75) Inventor: Ronald Richard Couts, Chesterfield, MI (US)

(73) Assignee: Ronald Richard Couts, Chesterfield, MI (US)

( * ) Notice: Subject to any disclaimer, the term of this patent is extended or adjusted under 35 U.S.C. 154(b) by 462 days.

(21) Appl. No.: 12/777,880

(22) Filed: May 11, 2010

(65) Prior Publication Data

US 2010/0326434 A1    Dec. 30, 2010

Related U.S. Application Data

(60) Provisional application No. 61/220,168, filed on Jun. 24, 2009.

(51) Int. Cl.
    *A62B 18/08* (2006.01)
    *A62B 9/04* (2006.01)
    *A45F 5/02* (2006.01)

(52) U.S. Cl.
    USPC ............ 128/207.17; 128/207.11; 128/206.27; 128/202.27; 128/200.24

(58) Field of Classification Search
    USPC ............. 128/200.24, 200.26, 202.27, 206.11, 128/206.13, 206.27, 207.11, 207.13, 207.14, 207.17, 207.18, DIG. 26; 24/336, 339, 10 R, 24/11 R, 11 P, 3.12, 11 CC, 329, 563, 11 HC; 604/174; 248/316.7; D2/891
    See application file for complete search history.

(56) References Cited

U.S. PATENT DOCUMENTS

| | | | | |
|---|---|---|---|---|
| 3,209,755 A | * | 10/1965 | McCarthy et al. | 604/174 |
| 3,780,209 A | * | 12/1973 | Schuplin | 174/51 |
| 4,774,946 A | * | 10/1988 | Ackerman et al. | 128/207.18 |
| 4,993,126 A | * | 2/1991 | Collins | 24/336 |
| 5,097,827 A | * | 3/1992 | Izumi | 128/207.18 |
| 5,829,103 A | * | 11/1998 | Allen | 24/11 R |
| 5,867,874 A | * | 2/1999 | Simpson | 24/336 |
| D412,611 S | * | 8/1999 | Simpson | D2/891 |
| 2005/0108857 A1 | * | 5/2005 | Wartian et al. | 24/10 R |

* cited by examiner

Primary Examiner — Annette Dixon

(57) ABSTRACT

An oxygen tubing holder may support oxygen tubing away from a person's ears by providing a clip that may attach to a hat, headband or the like. The oxygen tubing holder may be placed near the ears, thereby permitting standard oxygen tubing to be used with the oxygen tubing holder. The oxygen tubing holder may include a clip end for attaching onto, for example, a hat or headband, and a U-shaped tubing holding end.

9 Claims, 2 Drawing Sheets

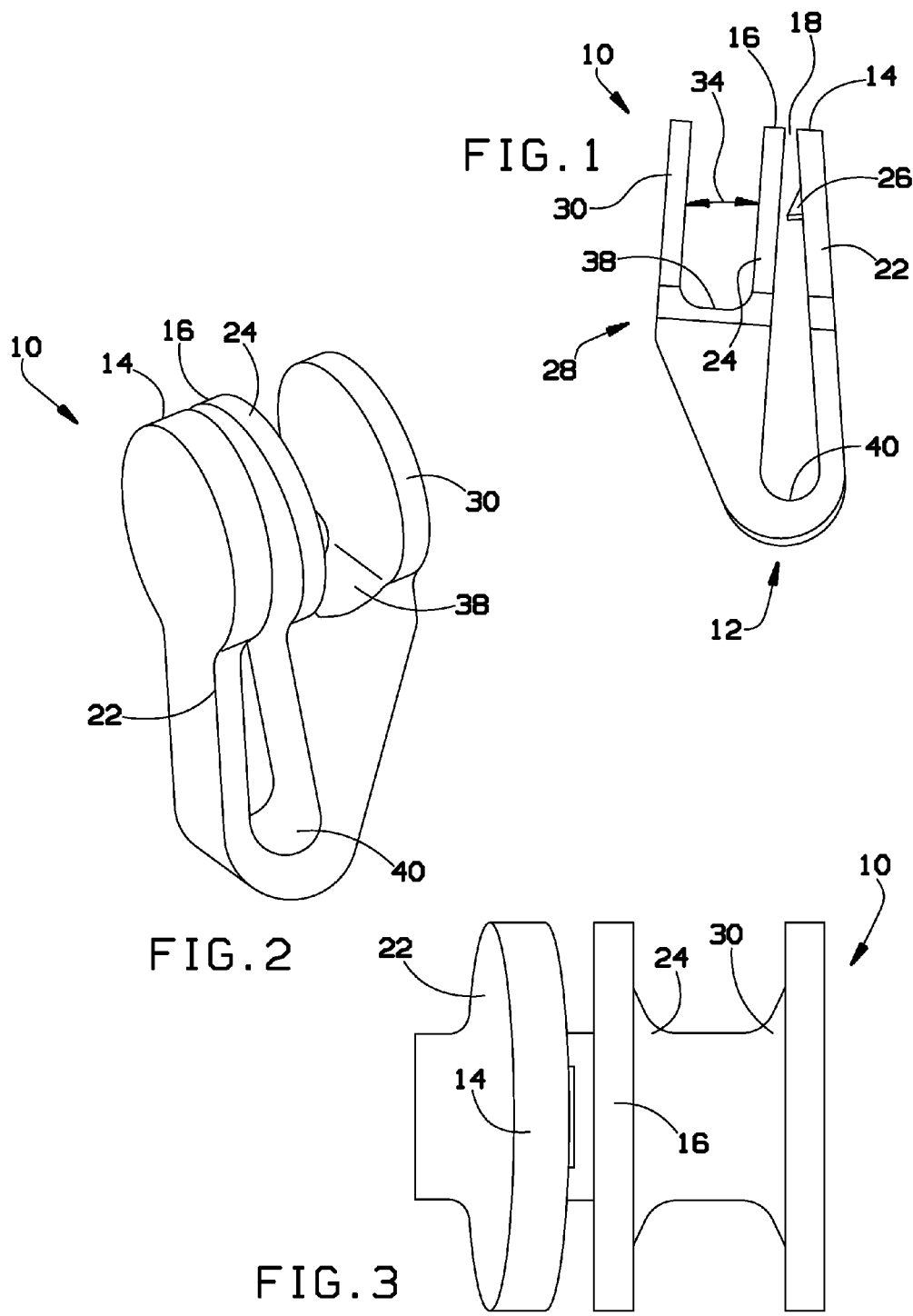

APPARATUS FOR ALLEVIATING PRESSURE ON EARS WHILE USING OXYGEN

CROSS-REFERENCE TO RELATED APPLICATIONS

This application claims the benefit of priority of U.S. Provisional patent application No. 61/220,168, filed Jun. 24, 2009, herein incorporated by reference.

BACKGROUND OF THE INVENTION

The present invention relates to oxygen use accessories and, more particularly, to a device and methods for alleviating pressure on the ears while using oxygen.

Oxygen is often administered to a patient via a nasal cannula. This is especially true for patients that may need continuous long-term oxygen therapy, such as patients suffering from chronic obstructive pulmonary disease (COPD). Typically, oxygen tubing may be routed around and behind a patient's ears to hold the oxygen delivery device in place.

Oxygen tubing placed over and around the ears may, over time, cause irritation to the patient's ears. For relief, the patient may need to find an alternative way to secure the oxygen tubing. Often, these alternative ways may be inconvenient or uncomfortable for the patient.

As can be seen, there is a need for an apparatus and methods for alleviating pressure on the ears of a person using oxygen.

SUMMARY OF THE INVENTION

In one aspect of the present invention, a oxygen tubing holder comprises first and second arms of a first U-shaped attachment end, the ends of the first and second arms disposed towards each other, the first arm flexibly separable from the second arm; and a third arm forming a second U-shaped tubing holding end with the second arm.

In another aspect of the present invention, a method for alleviating pressure on the ears of a user of oxygen comprises attaching at least one oxygen tubing holder onto a brim of headwear, the oxygen tubing holder having first and second arms of a first U-shaped attachment end, the ends of the first and second arms disposed towards each other, the first arm flexibly separable from the second arm, and a third arm forming a second U-shaped tubing holding end with the second arm; and running oxygen tubing through the tubing holding end, thereby reducing contact of the oxygen tubing from the ears of the user.

These and other features, aspects and advantages of the present invention will become better understood with reference to the following drawings, description and claims.

BRIEF DESCRIPTION OF THE DRAWINGS

FIG. 1 is a side view of the oxygen tubing holder according to an embodiment of the present invention;

FIG. 2 is a perspective view of the oxygen tubing holder of FIG. 1;

FIG. 3 is a top view of the oxygen tubing holder of FIG. 1;

DETAILED DESCRIPTION OF THE INVENTION

Figure 4:
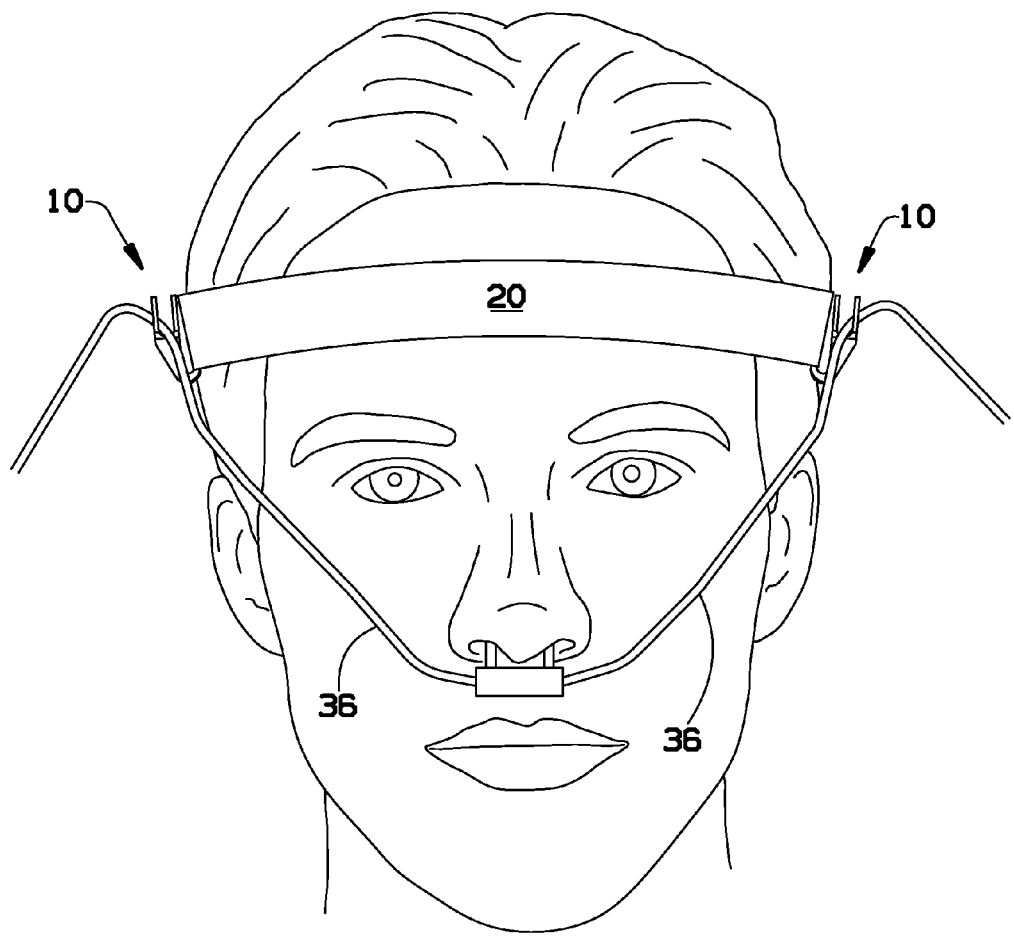
FIG. 4 is a perspective view of the oxygen tubing holder of FIG. 1 in use on a person according to an embodiment of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, an embodiment of the present invention provides a device and method for alleviating pressure on a person's ears while using oxygen. An oxygen tubing holder may support oxygen tubing away from a person's ears by providing a clip that may attach to a brim of a user's headwear, such as a hat, headband, visor or the like. The oxygen tubing holder may be placed near the ears, thereby permitting standard oxygen tubing to be used with the tubing holder of the present invention. The oxygen tubing holder may include a clip end for attaching onto, for example, a hat or headband, and a U-shaped tubing holding end.

Referring to FIGS. 1 through 4, an oxygen tubing holder 10 may be configured as a one-piece double U-shape. A first U-shaped end may be an attachment end 12. The ends 14, 16 of the U-shaped attachment end 12 may be pushed together so that the ends 14, 16 may almost touch. A space 18 between the ends 14, 16 may be large enough to fit the space 18 onto a brim of a hat, visor, headband 20 or the like.

At least one arm 22, 24 of the attachment end 12 may include a mechanism to help secure the tubing holder 10 onto the headband 20. In one embodiment, a ridged surface (not shown) may be disposed on the inside of the arms 22, 24. In another embodiment, at least one barb 26 may be disposed on the inside of at least one of the arms 22, 24. The arm 22 may be flexed away from the arm 24 to allow for attachment of the oxygen tubing holder 10 onto products (such as the headband 20) of various thicknesses.

A second U-shaped end may be a tubing holding end 28. The arms 24, 30 of the tubing holding end 28 may be substantially parallel to each other and may be separated by a distance 34 sufficient to hold the outside diameter of oxygen tubing 36. In one embodiment, the distance 34 may be designed to frictionally hold oxygen tubing in place during use of the oxygen tubing holder 10.

In one embodiment of the present invention, a bottom portion 38 of the tubing holding end 28 may be at a different height as compared to a bottom portion 40 of the attachment end. In one embodiment, the bottom portion 38 may be higher (when worn by a user) than the bottom portion 40.

The oxygen tubing holder 10 may be made of medical grade plastic. The oxygen tubing holder 10 may be made by an injection molding process. Other materials and processes for making the oxygen tubing holder 10 may be used as may be known in the art. The oxygen tubing holder 10 may be made of a latex-free material to avoid allergic reactions with the users.

In use, the user may secure the attachment end 12 of the oxygen tubing holder 10 onto a hat, headband, visor or the like. Typically, two oxygen tubing holders 10 may be used, attached to the hat, headband, visor, or the like, at a location corresponding generally to the location of the user's ears. When the hat, headband or visor is worn, the user may remove oxygen tubing from around their ears and place the oxygen tubing into the tubing holding end 28 of the oxygen tubing holder 10. This arrangement may allow the user to continue to receive oxygen while avoiding contact between the oxygen tubing and the user's ears.

The oxygen tubing holder 10 may be made of any suitable materials, typically plastic. The oxygen tubing holder 10 may be made of various colors, designs, patterns and the like.

It should be understood, of course, that the foregoing relates to exemplary embodiments of the invention and that modifications may be made without departing from the spirit and scope of the invention as set forth in the following claims.

What is claimed is:

1. An oxygen tubing holder comprising:
a first side of the oxygen tubing holder operable to receive oxygen tubing, the first side formed from a terminus of a first arm, a second arm, and a third arm, the terminus of the first arm, the second arm, and the third arm being substantially planar;
a first U-shape attachment end having a first bottom portion and the first and second arms extending from the first bottom portion and terminating at the first side of the oxygen tubing holder to form the first U-shaped attachment end, the ends of the first and second arms disposed towards each other, the first arm flexibly separable from the second arm; and
a second U-shape tubing holding end having a second bottom portion and the third arm extending from the second bottom portion, the third arm terminating at the first side of the oxygen tubing holder, and forming the second U-shaped tubing holding end with the second arm extending from the second bottom portion, wherein
a first opening between ends of the first and second arms of the first U-shape is accessible from the first side of the oxygen tubing holder, and
a second opening between ends of the second arm and the third arm of the second U-shape accessible from the first side of the oxygen tubing holder, adjacent to the first opening, wherein a first length of the second arm from its terminus to the first bottom portion is longer than a second length of the second arm from its terminus to the second bottom portion.

2. The oxygen tubing holder of claim 1, further comprising at least one barb disposed on an inside surface of at least one of the first and second arms.

3. The oxygen tubing holder of claim 1, further comprising one barb disposed on an inside surface of the first arm.

4. The oxygen tubing holder of claim 1, wherein the first and seconds arms have a space therebetween, the space adapted to receive a brim of a user's headwear.

5. The oxygen tubing holder of claim 1, wherein the second and third arms are substantially parallel to each other.

6. The oxygen tubing holder of claim 1, wherein a distance between the second and third arms is selected to frictionally hold an oxygen tubing.

7. A method for alleviating pressure on the ears of a user of oxygen, the method comprising:
attaching at least one oxygen tubing holder onto a brim of headwear, the oxygen tubing holder having a first side of the oxygen tubing holder operable to receive oxygen tubing, the first side formed from a terminus of a first arm, a second arm, and a third arm, the terminus of the first arm, the second arm, and the third arm being substantially planar, a first U-shape attachment end having a first bottom portion and the first and second arms extending from the first bottom portion and terminating at the first side of the oxygen tubing holder to form the first U-shaped attachment end, the ends of the first and second arms disposed towards each other, the first arm flexibly separable from the second arm, and a second U-shaped tubing holding end having a second bottom portion and the third arm extending from the second bottom portion and terminating at the first side of the oxygen tubing holder, forming the second U-shaped tubing holding end with the second arm extending from the second bottom portion, wherein a first opening between ends of the first and second arms of the first U shape is accessible from a first side of the oxygen tubing holder, and a second opening between ends of the second arm and the third arm of the second U-shape accessible from the first side of the oxygen tubing holder, adjacent to the first opening, wherein a first length of the second arm from its terminus to the first bottom portion is longer than a second length of the second arm from its terminus to the second bottom portion; and
running oxygen tubing through the tubing holding end, thereby reducing contact of the oxygen tubing from the ears of the user.

8. The method of claim 7, wherein two oxygen tubing holders are attached to the brim of the headwear, wherein the two oxygen tubing holders are disposed at a location near the user's ears.

9. The method of claim 7, further comprising securing the oxygen tubing holder to the brim of the headwear with at least one barb formed on an inside surface of at least one of the first and second arms.

* * * * *